United States Patent [19]

Berg

[11] 4,292,142

[45] Sep. 29, 1981

[54] SEPARATION OF ETHYLBENZENE FROM PARA- AND META-XYLENES BY EXTRACTIVE DISTILLATION

[75] Inventor: Lloyd Berg, Bozeman, Mont.

[73] Assignee: International Synthetic Rubber Co., Ltd., Southampton, England

[21] Appl. No.: 224,175

[22] Filed: Jan. 12, 1981

[51] Int. Cl.³ ............................................. F01D 3/40
[52] U.S. Cl. ...................................... 203/51; 585/805
[58] Field of Search ...................... 585/805, 807, 808; 203/50, 51, 57, 61

[56] References Cited

U.S. PATENT DOCUMENTS 2,431,655  11/1947  Amos et al. ........................... 203/51
2,945,902   7/1960  Romans .................................. 203/51

Primary Examiner—Frank Sever

[57] ABSTRACT

Ethylbenzene and para-xylene and/or meta-xylene are difficult to separate by distillation because they boil only 2.3 C.° and 3.1 C.° apart. Ethylbenzene can be readily separated from the xylenes by using extractive distillation in which the extractive distillation agent is a mixture of oxygen-containing organic compounds boiling higher than the xylenes. The mixture typically includes phthalic anhydride and maleic anhydride with or without a solvent.

18 Claims, No Drawings

SEPARATION OF ETHYLBENZENE FROM PARA- AND META-XYLENES BY EXTRACTIVE DISTILLATION

FIELD OF THE INVENTION

This invention relates to a method for separating ethylbenzene from the xylenes using mixtures of two or more compounds as extractive agents in extractive distillation.

DESCRIPTION OF THE PRIOR ART

Extractive distillation is the method of separating close boiling compounds by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus required either fewer plates to effect the same separation or make possible a greater degree of separation with the same number of plates. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixture and the extractive agent are continuously removed from the column. The usual methods of separation of these two components are the use of another rectification column, cooling and phase separation, or solvent extraction.

The separation of ethylbenzene from p-xylene and/or m-xylene by extractive distillation has been reported. Amir, U.S. Pat. No. 3,105,017 describes the use of single compounds to effect this separation and he prefers 1,2,4-trichlorobenzene. This compound increases the relative volatility from 1.06 to 1.116. Nixon, U.S. Pat. Nos. 2,532,031 and 2,638,441 reported that antimony trichloride gave a relative volatility of 1.15. Anstey, Brit. Pat. No. 1,257,024-5 used phosphazines to effect this separation. Berg & Kober, AIChE Journ., 26,862 (September 1980) and Berg, U.S. Pat. Appl. Ser. No. 929,929, Aug. 1, 1978 reported on the use of mixtures of polychloro compounds to effect this separation. They prefer mixtures of pentachlorophenol, 2,3,4,6-tetrachlorophenol, 1,2,4-trichlorobenzene, 1,2,3-trichlorobenzene, benzene hexachloride, 2,4-dichlorotoluene, 1,2,4,5-tetrachlorobenzene and polychlorobenzenes, some of these mixtures raising the apparent relative volatility to as high as 1.27.

The advantage of using extractive distillation in this separation can be seen from Table I below. To separate ethylbenzene from p-xylene in 99% purity by conventional rectification requires a minimum of 157 theoretical plates at total reflux, thus somewhat more at a finite reflux ratio. With an extractive distillation agent such as 1,2,4-trichlorobenzene, the relative volatility goes to 1.11 and only 87 plates are now required. The best extractive distillation agents that I have discovered push the relative volatility up to about 1.2 and Table I shows that they will reduce the plate requirement to 50 plates

TABLE I

Theoretical Plates Required vs. Relative Volatility for Ethylbenzene-p-Xylene Separation.

| Relative Volatility | Theor. Plates Req'd. at Total Reflux |
| --- | --- |
| 1.06 | 157 |
| 1.08 | 118 |
| 1.10 | 97 |
| 1.11 | 87 |
| 1.12 | 81 |
| 1.13 | 75 |
| 1.14 | 70 |
| 1.15 | 66 |
| 1.16 | 62 |
| 1.17 | 58 |
| 1.18 | 55 |
| 1.19 | 53 |
| 1.20 | 50 |

Extractive distillation typically requires the addition of an equal amount to twice as much extractive agent as close boiling compounds on each plate in the rectification column. The extractive distillation agent should be heated to about the same temperature as the plate into which it is introduced. Thus extractive distillation imposes an additional heat requirement on the column as well as somewhat larger diameter plates for the same production output. To be economically attractive, the extractive distillation system must save more in the reduction of the number of theoretical plates and the size of the column than it adds in the cost of larger plates and additional heat requirement. This will vary depending on the difficulty of the separation and the cost of heat. I found that in the separation of ethylbenzene from p-xylene and/or m-xylene, the extractive agent should increase the relative volatility to about 1.2 to make the process economically attractive under the equipment and heat costs in effect at the time of my investigation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. I recommend twenty Centigrade degrees or more difference.

Ethylbenzene is the major precursor to most processes for producing styrene. Styrene is used principally in plastics manufacture. In the preparation of high polymers, extreme purity is absolutely necessary. It is the presence of impurities that stops chain growth and prevents polymerization to the desired molecular weight. To make high purity styrene, it is necessary to use high purity ethylbenzene. Ethylbenzene is frequently found admixed with its isomers, the xylenes. Since ethylbenzene boils 2.3 C. degrees from p-xylene and 3.1 C. degrees from m-xylene, separation of ethylbenzene from these xylenes by conventional rectification to produce high purity ethylbenzene is almost impossible. One of the major sources of ethylbenzene is the $C_8$ fraction of hydroformed naphthenic petroleum and here the xylenes will be present with the ethylbenzene.

OBJECTIVE OF THE INVENTION

The object of this invention is to provide a process or method of extractive distillation that will enhance the apparent relative volatility of ethylbenzene and the xylenes in their separation in a rectification column. It is a particular object of this invention to identify suitable mixtures of oxygenated organic compounds which will increase the apparent relative volatility of ethylbenzene to p-xylene and/or m-xylene to about 1.2. It is a further object of this invention to identify oxygenated organic compounds which, in addition to the above constraints, are stable, can be separated from the xylenes by rectification with relatively few theoretical plates and can be recycled to the extractive distillation column and re-used with little decomposition.

SUMMARY OF THE INVENTION

The objects of this invention are provided by a process for separating ethylbenzene from p-xylene and/or m-xylene using a mixture of phthalic anhydride and maleic anhydride with or without an oxygen containing organic compound as a solvent, as the agent in extractive distillation.

DETAILED ELABORATION OF THE INVENTION

I have discovered that a mixture of approximately equal parts of phthalic anhydride and maleic anhydride when used as the agent in extractive distillation to separate ethylbenzene from p-xylene and/or m-xylene, will give a relative volatility of 1.21 when the amount of agent is between one and two parts per part of ethylbenzene-xylene mixture. When phthalic anhydride is used alone the relative volatility is 1.17, when maleic anhydride is used alone, the relative volatility is 1.13. Thus the mixture is considerably more effective than either the phthalic anhydride or the maleic anhydride when used alone.

Phthalic anhydride, maleic anhydride and phthalic anhydridemaleic anhydride mixtures melt so high that they freeze in the presence of ethylbenzene relatively close to the boiling point of ethylbenzene which is 136.15° C. at 760 mm.Hg. While this does not preclude the use of the phthalic anhydride-maleic anhydride mixture, there is an advantage in the ease of operation to adding a third component to the phthalic anhydride-maleic anhydride mixture to lower the freezing point.

Table II is a list of organic compounds which when added to phthalic anhydride-maleic anhydride mixtures in the amount of 15-25%, lower the relative volatility to less than 1.20. Table III is a list of those organic compounds which when added to the phthalic anhydride-maleic anhydride mixture in the amount of 15-25%, retain or increase the 1.20 relative volatility.

TABLE II

Compounds Which Do Not Enhance the Relative Volatility of Phthalic anhydride - Maleic Anhydride Mixtures.

| Compound | Compound |
| --- | --- |
| Acetoin | Glycerol laurate |
| Acetol | Glycerol monostearate |
| Acetyl methyl carbinol | Glycerol triacetate |
| Adipic acid | Glycol diacetate |
| Alkenyl succinic anhydride | Guaiacol |
| Anisic acid | Hexahydro-4-methyl phthalic anhydride |
| Anisolaldehyde | 1,6-Hexanediol |
| Anisyl alcohol | Hexanoic acid |
| Anisyl cyanide | Hexanol-1 |
| Benzanthrone | Hydratropic acid |
| 1,2,4-Benzene tricarboxylic acid anhydride | Hydroquinone |
| Benzhydrol | m-Hydroxyacetophenone |
| Benzil | p-Hydroxybenzoic acid |
| Benzilic acid | 2-Hydroxy-4-methoxy |

TABLE II-continued

Compounds Which Do Not Enhance the Relative Volatility of Phthalic anhydride - Maleic Anhydride Mixtures.

| Compound | Compound |
| --- | --- |
| 3,3',4,4'-Benzophenone tetra carboxylic acid anhydride | benzophenone |
| | Inositol |
| 2-Benzoylbenzoic acid | Isobutanol |
| Benzyl benzoate | Isobutyl butyrate |
| Benzyl cyanide | Isocetyl stearate |
| Benzyl ether | Isodecanol |
| o-Benzyl phenol | Isodibenzanthron |
| bis(dimethylamino)benzophenone | Isophthalic acid |
| | Isophthalonitrile |
| Bis-phenol A | Isopropyl benzoate |
| 1,4-Butanediol | Isopropyl palmitate |
| 2,3-Butanedione monoxime | o-Isopropyl phenol |
| n-Butanol | m-Isopropyl phenol |
| p-tert.Butyl benzoic acid | p-Isopropyl phenol |
| Butyl butyrate | Lactic acid |
| Butyl carbinol acetate | Levulinic acid |
| t-Butyl catechol | Linalool |
| Butyl cyclohexyl phthalate | Malic acid |
| n-Butyl ether | Malononitrile |
| 2-n-Butyl-2-ethyl-1,3-propanediol | Mandelic acid |
| | 3-Mercaptopropionic acid |
| Butyl lactate | Methyl acetoacetate |
| 2-t-Butyl-4-methylphenol | Methyl amyl ketone |
| 2-t-Butyl-6-methylphenol | a-Methyl benzyl alcohol |
| 4-sec. Butylphenol | 2-Methyl-1-butanol |
| 1,3-Butylene glycol | 3-Methyl-1-butanol |
| gamma-Butyrolactone | Methyl bis-phenol acetate |
| n-Butyronitrile | Methyl chavicol |
| e-Caprolactam | Methyl glutaronitrile |
| e-Caprolactone | Methyl hexahydro phthalic acid anhydride |
| Catechol | |
| Cetyl palmitate | Methyl hydratropate |
| Cinnamic acid | Methyl-p-hydroxy benzoate |
| Cinnamyl alcohol | Methyl isoamyl ketone |
| Citronellol | 3-Methyl-2-nitro phenol |
| p-Cresol | 4-Methyl-2-nitro phenol |
| Cyclododecanol | Methyl salicylate |
| Cyclohexanol | 3-Methyl sulfolene |
| Cyclohexanone | 4-Methyl tetrahydroxy phthalic anhydride |
| cis-4-Cyclohexene-1,2-dicarboxylic acid | |
| | 1,2-Methylene dioxybenzene |
| n-Decanol | 2-Methoxyethyl acetate |
| n-Decyl methyl sulfoxide | 4-Methoxy-4-methyl pentanone |
| Diacetone alcohol | Morpholine |
| 2,4-di-t-Amyl phenol | Naphthol-1 |
| Dibenzanthrone | Naphthol-2 |
| Dibutyl adipate | Neodecanoic acid |
| 4,6-di-t-Butyl catechol | Neopentanoic acid |
| Dibutyl ether | Neopentyl glycol |
| Dibutyl phthalate | Nitrobenzene |
| Dibutyl tartrate | p-Nitrobenzoic acid |
| Dicyanodiamide | 2-Nitrobiphenyl |
| Diethyl adipate | 3-Nitro-2-butanol |
| Diethyl carbonate | 5-Nitroisophthalic acid |
| Diethyl malonate | 5-Nitroisophthalic acid mono ethyl ether |
| Diethyl oxalate | |
| Diethyl succinate | 5-Nitro diethyl phthalate |
| Diethyl tartrate | 2-Nitrophenol |
| Diethylene glycol | 2-Nitropropane |
| Diethylene glycol butyl ether | 2-Nitrotoluene |
| Diethylene glycol diethyl ether | 3-Nitrotoluene |
| Diethylene glycol ethyl ether | 2-Nitro-m-xylene |
| Diethylene glycol ethyl ether acetate | 3-Nitro-o-xylene |
| | 4-Nitro-o-xylene |
| Diethylene glycol hexyl ether | Nonyl alcohol |
| Dihexyl phthalate | Octadecenyl succinic anhydride |
| Dihydroterpineol | Octanol-1 |
| Dihexyl phthalate | 1,5-Pentanediol |
| Dihydroanisole | 2,4-Pentanedione |
| Dihydroxyacetone | n-Pentanol |
| Dihydroxy diphenyl sulfone | 3-Pentanone |
| Diisobutyl carbinol | Pentyl propionate |
| Diisobutyl ketone | Perylene-3,4,9,10-tetracarboxylic acid dianhydride |
| Diisobutyl phthalate | |
| Diisodecyl phthalate | a-Phenyl ethanol |
| Diisononyl adipate | Phenyl glycidyl ether |
| Diisononyl phthalate | 4-Phenyl phenol |
| | Phenyl salicylate |

TABLE II-continued

Compounds Which Do Not Enhance the Relative Volatility of Phthalic anhydride - Maleic Anhydride Mixtures.

| Compound | Compound |
|---|---|
| Diisooctyl phthalate | Phenyl sulfone |
| Dihydro linalool | Phthalic acid |
| N,N-Dimethyl acetamide | Phthalimide |
| Dimethyl adipate | Pinanol |
| Dimethyl glutarate | Propiophenone |
| Dimethyl maleate | Propylene glycol |
| 2,6-Dimethyl-4-heptanone | Propylene glycol isobutyl ether |
| 2,3-Dimethyl phenol | Propylene glycol mono stearate |
| 2,4-Dimethyl phenol | Pyrogallol |
| 2,5-Dimethyl phenol | Pyruvic acid |
| 2,6-Dimethyl phenol | Resorcinol |
| 3,4-Dimethyl phenol | Salicylaldehyde |
| Dimethyl phthalate | Salicylic acid |
| Dimethyl terephthalate | Succinic acid |
| Dioctyl phthalate | 4,4'-Sulfonyl diphenol |
| 1,1-Diphenyl acetone | Tartaric acid |
| Diphenyl ether | Terephthalic acid |
| Dipropyl adipate | Terpinyl acetate |
| Dipropylene glycol | 1,2,3,6-Tetrahydrobenzaldehyde |
| Dipropylene glycol methyl ether | Tetrahydrophthalic acid |
| | 1,4,9,10-Tetrahydroanthracene |
| Dodecanedioic acid | a-Tetralone |
| Dodecenyl succinic acid | 4,4'-Thiodiphenol |
| p-Ethyl benzaldehyde | Thioglycolic acid |
| Ethyl benzoate | Thiophenol |
| 2-Ethyl butanol | Thiopropionic acid |
| Ethyl-p-hydroxy benzoate | Thiosalicylic acid |
| Ethylene glycol | Thiourea |
| Ethylene glycol butyl ether acetate | Thymol |
| | m-Toluic acid |
| Ethylene glycol diacetate | p-Toluic acid |
| Ethylene glycol hexyl ether | p-Toluyl benzoic acid |
| Ethylene glycol methyl ether acetate | Tricresyl phosphate |
| | Triethyl phosphate |
| Ethylene glycol phenyl ether | Triethylene glycol |
| Eugenol | 1,2,6-Trihydroxyhexane |
| o-Fluoroaniline | Trimethyl acetic acid |
| Formamide | 3,4,5-Trimethoxy benzoic acid |
| Furfuryl alcohol | Trimethyl phosphate |
| Geraniol | Tripropylene glycol |
| Glutaric anhydride | 2-Undecanone |
| Glycerol | Undecyl alcohol |
| Glycerol dilaurate | Vanillin |

TABLE III

Compounds Which Enhance the Relative Volatility of Phthalic anhydride - Maleic anhydride mixtures.

| Compound | Compound |
|---|---|
| Acetonylacetone | Ethylene glycol ethyl ether acetate |
| Acetophenone | |
| Acetyl salicylic acid | Ethylene glycol mono stearate |
| Adiponitrile | Fenchyl alcohol |
| p-tert. Amyl phenol | 9-Fluorenone |
| Anisole | 1,6-Hexanediol |
| Azelaic acid | Hexahydrophthalic acid anhydride |
| Benzaldehyde | |
| Benzoic acid | Hexyl acetate |
| Benzonitrile | Hexylene glycol |
| Benzophenone | Hexylene glycol diacetate |
| Benzyl acetate | Hydro bis-phenol A |
| Benzyl alcohol | Isoborneol |
| Butoxypropanol | Isobornyl acetate |
| Butyl benzyl phthalate | Isobornyl methyl ether |
| o-sec. Butyl phenol | Isooctanol |
| 2-tert. Butyl phenol | Isophorone |
| 3-tert. Butyl phenol | Isopropyl myristate |
| 4-tert. Butyl phenol | Linalyl acetate |
| 1,3-Butylene glycol | Menthyl acetate |
| b-Butyrolactone | Methyl benzoate |
| Carbitol acetate | 4-Methyl benzophenone-2-carboxylic acid |
| Citronellyl acetate | |
| m-Cresol | Methyl hexanoate |
| o-Cresol | Myristic acid |
| Cuminaldehyde | m-Nitroacetophenone |
| Cyanoacetic acid | p-Nitroacetophenone |
| Decanoic acid | m-Nitrobenzaldehyde |

TABLE III-continued

Compounds Which Enhance the Relative Volatility of Phthalic anhydride - Maleic anhydride mixtures.

| Compound | Compound |
|---|---|
| Dibenzo furan | m-Nitrobenzoic acid |
| 2,6-di-tert.Butyl-p-cresol | 5-Nitroisophthalic acid diethyl ester |
| Dibutyl ether | |
| 2,5-di-tert-Butyl hydroquinone | p-Nitrophenol |
| 2,6-di-tert.Butyl phenol | p-Nitrophenylacetic acid |
| Diethyl maleate | p-Nitrotoluene |
| Diethyl malonate | Nonanic acid |
| Diethyl phenyl malonate | 2-Octanone |
| Diethyl phthalate | Phenethyl alcohol |
| Diethyl succinate | Phenol |
| Diethylene glycol butyl ether acetate | Phenyl acetate |
| | Phenyl acetic acid |
| Diethylene glycol dimethyl ether | 2-Phenyl phenol |
| Diethylene glycol methyl ether | 3-Phenyl-1-propanol |
| Dihydroterpinyl acetate | Propionic anhydride |
| Diisobutyl ketone | Propoxypropanol |
| Dimethyl formamide | Propyl-p-hydroxybenzoate |
| 3,5-Dimethyl phenol | Sebacic acid |
| Dimethyl succinate | Succinic anhydride |
| Dimethyl sulfone | Succinimide |
| Dimethyl sulfoxide | Sulfolane |
| Ethyl acetoacetate | Sulfolene |
| 2-Ethyl butyric acid | Tetrahydrofurfuryl alcohol |
| 2-Ethylhexanol | 2,2',4,4'-Tetrahydroxybenzophenone |
| Ethyl hexyl acetate | |
| p-Ethyl phenol | p-Tolualdehyde |
| Ethyl phenyl acetate | Tributyl phosphate |
| Ethyl salicylate | Triethylene glycol diacetate |
| Ethylene glycol butyl ether | o-Toluic acid |

I have discovered several combinations of organic compounds which do not fit the categories phthalic anhydride-maleic anhydride-solvent and they are listed in Table IV.

TABLE IV

Mixtures That Enhance the Separation of Ethylbenzene from Xylenes by Extractive Distillation.

| Mixture |
|---|
| Phthalic anhydride, Benzoic acid, Diisononyl phthalate |
| Phthalic anhydride, Benzoic acid, Diethylene glycol ethyl ether acetate |
| Phthalic anhydride, Benzoic acid, Methyl salicylate |
| Phthalic anhydride, Benzoic acid |
| Phthalic anhydride, Benzoic acid, Diisobutyl ketone |
| Phthalic anhydride, Benzoic acid, Diisononyl phthalate |
| Phthalic anhydride, Benzoic acid, Diisobutyl phthalate |
| Phthalic anhydride, Benzoic acid, Diethyl maleate |
| Phthalic anhydride, Benzoic acid, Methyl hexanoate |
| Phthalic anhydride, Benzoic acid, Isobutyl isobutyrate |
| Phthalic anhydride, Benzoic acid, Dimethylsulfoxide |
| Phthalic anhydride, Salicylic acid, Diisobutyl phthalate |
| Phthalic anhydride, Salicylic acid, Methyl hexanoate |
| Phthalic anhydride, Salicylic acid, Ethylene glycol phenyl ether |
| Phthalic anhydride, Salicylic acid, Dimethylsulfoxide, Methyl hexanoate |
| Phthalic anhydride, Benzoic acid, Dimethylsulfoxide, Methyl hexanoate |
| Phthalic anhydride, Succinic acid, Ethylene glycol diacetate, Carbitol acetate |
| Benzoic acid, Succinic anhydride, Diethyl maleate |
| Benzoic acid, Maleic anhydride, Diethyl maleate |
| Benzoic acid, Maleic anhydride, Methyl hexanoate |
| Benzoic acid, Maleic anhydride, Acetophenone |
| Benzoic acid, Phthalic anhydride, Dimethylformamide |
| Benzoic acid, Maleic anhydride, Triethylene glycol diacetate |
| Benzoic acid, Maleic anhydride, Diethylene glycol hexyl ether |
| Benzoic acid, Maleic anhydride, Dimethylphthalate |
| Benzoic acid, Maleic anhydride, Dibutylphthalate |
| Benzoic acid, Phthalic anhydride, n-Octanol |
| Benzoic acid, Phthalic anhydride, n-Decanol |
| Benzoic acid, Maleic anhydride, Diisononyl adipate |
| Phthalic anhydride, Methyl p-hydroxybenzoate, Diethyloxalate |
| Benzoic acid, Maleic anhydride, Tributyl phosphate |
| Benzoic acid, Phthalic anhydride, Maleic anhydride, Glycerol triacetate |

TABLE IV-continued
Mixtures That Enhance the Separation of Ethylbenzene from Xylenes by Extractive Distillation.

Mixture

Benzoic acid, Phthalic anhydride, Maleic anhydride, Diethyl maleate
Benzoic acid, Phthalic anhydride, Maleic anhydride, Phenyl acetate
Benzoic acid, Salicylic acid, Tributyl phosphate
Benzoic acid, Maleic anhydride, n-Octanol
Benzoic acid, Phthalic anhydride, Maleic anhydride, Ethylene glycol diacetate
Benzoic acid, Phthalic anhydride, Maleic anhydride, Dimethyl adipate
Benzoic acid, Phthalic anhydride, Maleic anhydride, Ethylene glycol methyl ether acetate
Benzoic acid, Phthalic anhydride, Maleic anhydride, Diethylene glycol diethyl ether
Benzoic acid, Phthalic anhydride, Maleic anhydride, Tributyl phosphate
Benzoic acid, Phthalic anhydride, Maleic anhydride, Tricresyl phosphate
Benzoic acid, Phthalic anhydride, Maleic anhydride, Catechol
Benzoic acid, Phthalic anhydride, Ethyl acetoacetate
Benzoic acid, Phthalic anhydride, Maleic anhydride, Ethyl acetoacetate
Benzoic acid, Phthalic anhydride, Ethyl acetoacetate
Benzoic acid, Maleic anhydride, 1,6-Hexanediol
Hexahydrophthalic anhydride, Maleic anhydride, Butoxypropanol
Hexahydrophthalic anhydride, Maleic anhydride, n-Octanol
Benzoic acid, Phthalic anhydride, Maleic anhydride, Phenol
Benzoic acid, Phthalic anhydride, Maleic anhydride, o-Cresol
Benzoic acid, Phthalic anhydride, Maleic anhydride, 2,6-Dibutyl phenol
Benzoic acid, Phthalic anhydride, Maleic anhydride, Diisobutyl ketone
Benzoic acid, Phthalic anhydride, Maleic anhydride, Tetrahydro furfuryl alcohol
Benzoic acid, Phthalic anhydride, 4-Nitro phenol
Benzoic acid, Phthalic anhydride, 4-tert. Butyl catechol
Benzoic acid, Maleic anhydride, 4-sec. Butyl phenol
Benzoic acid, Phthalic anhydride, 4-tert. Butyl phenol
Maleic anhydride, m-Nitrobenzoic acid, Butoxypropanol
Phthalic anhydride, Levulinic acid
Benzoic acid, Phthalic anhydride, Dimethyl sulfone
Maleic anhydride, 4-tert. Butyl catechol, Nonanic acid
Azelaic acid, Maleic anhydride, Ethylphenyl acetate
Azelaic acid, Maleic anhydride, Phenylacetic acid
Phthalic anhydride, Acetylsalicylic acid, Isophorone
Azelaic acid, Phthalic anhydride, Isophorone
Benzoic acid, Phthalic anhydride, 2-Phenylphenol
Maleic anhydride, 2-Phenylphenol, Isobornyl acetate
Benzoic acid, Maleic anhydride, p-Ethylbenzaldehyde
Phthalic anhydride, o-Toluic acid, Phenol
Maleic anhydride, p-Nitrophenol, Myristic acid
Phthalic anhydride, m-Nitrobenzoic acid
Phthalic anhydride, Acetonylacetone
Maleic anhydride, m-Nitroacetophenone The question might be asked, are three or four components really necessary or would one or two of them serve as well. The answer to this question is presented in Table V. It lists the relative volatility of a number of the three component systems and the relative volatility of each binary combination as well as the relative volatility of the solvent. Note that the relative volatility of phthalic anhydride is 1.17, of maleic anhydride, 1.13. The relative volatility of the phthalic anhydride-maleic anhydride mixture is 1.22. In every case in Table V the ratios of the solvent to the ethylbenzene-xylene mixture is 1 and 1.5, of the binary combinations ½:½ and ¾:¾ per part of ethylbenzene-xylene and the phthalic anhydride-maleic anhydride-solvent is 0.4:0.4:0.2 and 0.6:0.6:0.3 per part of ethylbenzene-xylene. To evaluate the data shown in Table V, consider the first solvent, o-toluic acid. The mixture phthalic anhydride-maleic anhydride-o-toluic acid has a relative volatility of 1.20. Phthalic anhydride-o-toluic acid is 1.10 and 1.12, maleic anhydride-o-toluic acid is 1.11 and 1.12 and o-toluic acid alone is 1.17 and 1.11. Thus the three component mixture is considerably more effective than any of its components used singularly or in binary combinations. Table V shows this comparison for several of the solvents that are part of this invention.

TABLE V
Relative Volatility of Single Component, Binary and Ternary Mixtures as Extractive Distillation Agents.

| Solvent, name | o-Toluic acid | | Isophorone | | Isobornyl acetate | |
|---|---|---|---|---|---|---|
| Solvent | 1.17 | 1.11 | 1.08 | 1.06 | 1.10 | 1.04 |
| Phthalic anhydride, Solvent | 1.10 | 1.12 | 1.11 | 1.08 | 1.10 | 1.11 |
| Maleic anhydride, Solvent | 1.11 | 1.12 | 1.16 | 1.09 | 1.09 | 1.15 |
| Ph. anh., Mal. anh., Solvent | 1.20 | 1.20 | 1.14 | 1.21 | 1.25 | 1.22 |

| Solvent, name | Propionic anhydride | | Anisole | | p-tert. Amyl phenol | | Isoborneol | |
|---|---|---|---|---|---|---|---|---|
| Solvent | 1.02 | 1.04 | 1.15 | 1.09 | 1.16 | 1.07 | 1.08 | 1.06 |
| Ph. anh., Solvent | 1.12 | 1.15 | 1.12 | 1.12 | 1.10 | 1.07 | 1.10 | 1.10 |
| Mal. anh., Solvent | 1.18 | 1.16 | 1.10 | 1.13 | 1.08 | 1.12 | 1.11 | 1.10 |
| Ph. anh, Mal. anh, Solvent | 1.21 | 1.21 | 1.18 | 1.18 | 1.23 | 1.21 | 1.21 | 1.23 |

| Solvent, name | Adiponitrile | | Methyl benzoate | | Diethyl maleate | | Bu benzyl phthalate | |
|---|---|---|---|---|---|---|---|---|
| Solvent | 1.05 | 1.09 | 1.07 | 1.08 | 1.07 | 1.09 | 1.10 | 1.18 |
| Ph. anh, Solvent | 1.15 | 1.12 | 1.12 | 1.15 | 1.08 | 1.08 | 1.06 | 1.09 |
| Mal. anh, Solvent | 1.07 | 1.14 | 1.09 | 1.07 | 1.08 | 1.03 | 1.17 | 1.10 |
| Ph. anh, Mal. anh, Solvent | 1.25 | 1.19 | | | 1.17 | 1.21 | 1.21 | 1.23 |

| Solvent, name | DiEtglycol diEtether | | Benzyl acetate | | Phenyl acetate | | Hexyl acetate | |
|---|---|---|---|---|---|---|---|---|
| Solvent | 1.05 | 1.10 | 1.03 | 1.04 | 1.05 | 1.06 | 1.05 | 1.08 |
| Ph. anh, Solvent | 1.04 | 1.10 | 1.12 | 1.09 | 1.15 | 1.09 | 1.12 | 1.15 |
| Mal. anh, Solvent | 1.18 | 1.11 | 1.06 | 1.09 | 1.12 | 1.06 | 1.11 | 1.15 |
| Ph. anh, Mal. anh, Solvent | 1.22 | 1.20 | 1.20 | 1.21 | 1.20 | 1.21 | 1.23 | 1.21 |
| | 2,6-dit-Bu | | 2,5-di.t-Bu | | EtHexyl | | 3,5-Dimethyl | |

TABLE V-continued
Relative Volatility of Single Component, Binary and Ternary Mixtures as Extractive Distillation Agents.

| Solvent, name | p-cresol | | hydroquinone | | acetate | | phenol | |
|---|---|---|---|---|---|---|---|---|
| Solvent | 1.06 | 1.03 | Will not dis. | | 1.15 | 1.15 | 1.13 | 1.05 |
| Ph. anh, Solvent | 1.18 | 1.07 | 1.16 | 1.17 | 1.15 | 1.09 | 1.17 | 1.08 |
| Mal. anh, Solvent | 1.12 | 1.10 | 1.12 | 1.07 | 1.06 | 1.02 | 1.09 | 1.13 |
| Ph. anh, Mal. anh, Solvent | 1.23 | 1.20 | 1.23 | 1.23 | 1.22 | 1.23 | 1.17 | 1.21 |

| Solvent, name | Et gly Bu ether acet. | | Et glycol diacetate | | Glycerol triacetate | | Myristic acid | |
|---|---|---|---|---|---|---|---|---|
| Solvent | 1.04 | 1.10 | 1.12 | 1.12 | 1.10 | 1.04 | 1.16 | 1.17 |
| Ph. anh, Solvent | 1.11 | 1.09 | 1.17 | 1.07 | 1.11 | 1.12 | 1.10 | 1.12 |
| Mal. anh, Solvent | 1.08 | 1.11 | 1.13 | 1.14 | 1.14 | 1.07 | 1.14 | 1.11 |
| Ph. anh, Mal. anh, Solvent | 1.21 | 1.21 | 1.23 | 1.20 | 1.20 | 1.20 | 1.22 | 1.23 |

| Solvent, name | Acetophenone | | Hex. glycol diacetate | | TriEt glycol diacetate | | Et glycol butyl ether | |
|---|---|---|---|---|---|---|---|---|
| Solvent | 1.17 | 1.08 | 1.05 | 1.07 | 1.07 | 1.06 | 1.17 | 1.09 |
| Ph. anh, Solvent | 1.13 | 1.11 | 1.09 | 1.10 | 1.07 | 1.12 | 1.12 | 1.09 |
| Mal. anh, Solvent | 1.11 | 1.10 | 1.11 | 1.11 | 1.10 | 1.09 | 1.08 | 1.06 |
| Ph. anh, Mal. anh, Solvent | 1.16 | 1.19 | 1.23 | 1.22 | 1.15 | 1.22 | 1.18 | 1.20 |

| Solvent, name | n-Octanol | | Diethyl oxalate | | Me p-OH benzoate | | Butoxy- propanol | |
|---|---|---|---|---|---|---|---|---|
| Solvent | 1.12 | 1.06 | 1.06 | 1.06 | 1.12 | 1.10 | 1.13 | 1.05 |
| Ph. anh, Solvent | 1.05 | 1.12 | 1.04 | 1.09 | 1.14 | 1.16 | 1.10 | 1.07 |
| Mal. anh, Solvent | 1.06 | 1.03 | 1.10 | 1.06 | 1.11 | 1.15 | 1.17 | 1.18 |
| Ph. anh, Mal. anh, Solvent | 1.19 | 1.23 | 1.21 | 1.22 | 1.20 | 1.22 | 1.19 | 1.22 |

| Solvent, name | Propoxy- propanol | | Catechol | | Ethyl aceto- acetate | | 2-Octanone | |
|---|---|---|---|---|---|---|---|---|
| Solvent | 1.07 | 1.05 | 1.07 | 1.03 | 1.08 | 1.04 | 1.09 | 1.10 |
| Ph. anh, Solvent | 1.07 | 1.14 | 1.09 | 1.06 | 1.15 | 1.15 | 1.15 | 1.13 |
| Mal. anh, Solvent | 1.04 | 1.12 | 1.14 | 1.08 | 1.08 | 1.09 | 1.02 | 1.11 |
| Ph. anh, Mal. anh, Solvent | 1.19 | 1.19 | 1.23 | 1.21 | 1.20 | 1.21 | 1.20 | 1.20 |

| Solvent, name | Benzyl alc. | | Phenethyl alcohol | | Phenol | | Benzo- phenone | |
|---|---|---|---|---|---|---|---|---|
| Solvent | 1.13 | 1.08 | 1.08 | 1.04 | 1.09 | 1.07 | 1.04 | 1.08 |
| Ph. anh, Solvent | 1.11 | 1.13 | 1.10 | 1.13 | 1.13 | 1.07 | 1.07 | 1.14 |
| Mal. anh, Solvent | 1.11 | 1.08 | 1.09 | 1.14 | 1.11 | 1.09 | 1.13 | 1.03 |
| Ph. anh, Mal. anh, Solvent | 1.19 | 1.19 | 1.21 | 1.22 | 1.20 | 1.20 | 1.19 | 1.20 |

| Solvent, name | p-Ethyl phenol | | Dibenzo- furan | | m-Nitro benz. acid | | o-sec.Bu phenol | |
|---|---|---|---|---|---|---|---|---|
| Solvent | 1.07 | 1.10 | 1.04 | 1.11 | m.p. too high | | 1.13 | 1.05 |
| Ph. anh, Solvent | 1.15 | 1.17 | 1.18 | 1.05 | 1.24 | 1.22 | 1.11 | 1.09 |
| Mal. anh, Solvent | 1.17 | 1.11 | 1.18 decomp. | | 1.10 | 1.12 | 1.10 | 1.15 |
| Ph. anh, Mal. anh, Solvent | 1.20 | 1.22 | 1.21 | 1.21 | 1.22 | 1.20 | 1.21 | 1.21 |

| Solvent, name | 2-tert. Bu phenol | | DiEt glycol diMe ether | | Hydro bis phenol A | | Phenyl acetic acid | |
|---|---|---|---|---|---|---|---|---|
| Solvent | 1.15 | 1.11 | 1.05 | 1.10 | 1.10 | 1.18 | 1.03 | 1.09 |
| Ph. anh, Solvent | 1.08 | 1.04 | 1.04 | 1.10 | 1.06 | 1.09 | 1.13 | 1.09 |
| Mal. anh, Solvent | 1.15 | 1.15 | 1.18 | 1.11 | 1.17 | 1.10 | 1.17 | 1.13 |
| Ph. anh, Mal. anh, Solvent | 1.20 | 1.21 | 1.22 | 1.20 | 1.21 | 1.23 | 1.21 | 1.22 |

| Solvent, name | Cuminalde- hyde | | Butyro- lactone | | Acetonyl acetone | | 4-Nitro toluene | |
|---|---|---|---|---|---|---|---|---|
| Solvent | 1.07 | 1.10 | 1.04 | 1.08 | 1.18 | 1.13 | 1.07 | 1.09 |
| Ph. anh, Solvent | 1.14 | 1.13 | 1.12 | 1.09 | 1.18 | 1.21 | 1.11 | 1.12 |
| Mal. anh, Solvent | 1.09 | 1.06 | 1.17 | 1.14 | 1.16 | 1.10 | 1.09 | 1.13 |
| Ph. anh, Mal. anh, Solvent | 1.20 | 1.20 | 1.18 | 1.22 | 1.20 | 1.20 | 1.22 | 1.21 |

| Solvent, name | Isopropyl myristate | | m-Nitrobenz- aldehyde | | Isobornyl Me ether | | m-Nitro acetophenone | |
|---|---|---|---|---|---|---|---|---|
| Solvent | 1.06 | 1.09 | 1.02 | 1.06 | 1.14 | 1.14 | 1.17 | 1.10 |
| Ph. anh, Solvent | 1.11 | 1.04 | 1.15 | 1.18 | 1.13 | 1.16 | 1.10 | 1.05 |
| Mal. anh, Solvent | 1.17 | 1.05 | 1.14 | 1.11 | 1.10 | 1.08 | 1.20 | 1.24 |
| Ph. anh, Mal. anh, Solvent | 1.22 | 1.23 | 1.22 | 1.22 | 1.22 | 1.23 | 1.25 | 1.20 |

| Solvent, name | 4-Nitro phenol | | 2-Phenyl phenol | | 2-Undeca- none | | Benzaldehyde | |
|---|---|---|---|---|---|---|---|---|
| Solvent | 1.16 | 1.12 | 1.05 | 1.05 | 1.04 | 1.06 | 1.13 | 1.10 |
| Ph. anh, Solvent | 1.17 | 1.08 | 1.09 | 1.18 | 1.11 | 1.15 | 1.17 | 1.13 |
| Mal. anh, Solvent | 1.15 | 1.13 | 1.11 | 1.11 | 1.07 | 1.12 | 1.16 | 1.13 |
| Ph. anh, Mal. anh, Solvent | 1.23 | 1.23 | 1.21 | 1.21 | 1.21 | 1.20 | 1.20 | 1.21 |

| Solvent, name | Diethyl phenylmal. | | p-Ethyl benzaldehyde | | Dimethyl succinate | | 9-Fluorenone | |
|---|---|---|---|---|---|---|---|---|
| Solvent | 1.09 | 1.08 | 1.03 | 1.10 | 1.07 | 1.10 | 1.09 | 1.17 |

TABLE V-continued
Relative Volatility of Single Component, Binary and Ternary Mixtures as Extractive Distillation Agents.

| | | | | | | | | |
|---|---|---|---|---|---|---|---|---|
| Ph. anh, Solvent | 1.15 | 1.05 | 1.16 | 1.06 | 1.16 | 1.16 | 1.09 | 1.05 |
| Mal. anh, Solvent | 1.08 | 1.14 | 1.17 | 1.05 | 1.16 | 1.12 | 1.13 | 1.17 |
| Ph. anh, Mal. anh, Solvent | 1.21 | 1.22 | 1.20 | 1.19 | 1.22 | 1.20 | 1.21 | 1.22 |

THE USEFULNESS OF THE INVENTION

The usefulness or utility of this invention can be demonstrated by referring to the data presented in Tables I, III and V. When ethylbenzene is separated from p-xylene by rectification in 99% purity, 157 theoretical plates are required at total reflux, somewhat more under a finite reflux ratio. Table III and V show that a mixture of phthalic anhydride, maleic anhydride and 2-octanone change the relative volatility to 1.20. From Table I it is apparent that now only 50 theoretical plates will be required to effect the separation of ethylbenzene from p-xylene in 99% purity.

WORKING EXAMPLES

EXAMPLE 1

A mixture comprising 50 grams of ethylbenzene and 50 grams of p-xylene was charged to an Othmer vapor-liquid equilibrium still and refluxed for six hours. Samples of the vapor and liquid were removed and analysed by gas chromatography. The vapor contained 51.0% ethylbenzene and 49.0% p-xylene, the liquid 49.5% ethylbenzene and 50.5% p-xylene. This indicates a relative volatility of ethylbenzene to p-xylene of 1.06. This has been confirmed by numerous other investigators.

EXAMPLE 2

A mixture comprising 50 grams of ethylbenzene and 50 grams of m-xylene was charged to the Othmer vapor-liquid equilibrium still and refluxed for six hours. Samples of the vapor and liquid were removed and analysed. The vapor contained 51.2% ethylbenzene and 48.8% m-xylene, the liquid 49.3% ethylbenzene and 50.7% m-xylene. This indicates a relative volatility of ethylbenzene to m-xylene of 1.08. This too is the value reported in the literature.

EXAMPLE 3

A mixture comprising 25 grams ethylbenzene, 25 grams p-xylene, 20 grams phthalic anhydride, 20 grams maleic anhydride and 10 grams isobornyl acetate was charged to the vapor-liquid equilibrium still and refluxed for twelve hours. Analyses indicated a vapor composition of 53.0% ethylbenzene 47.0% p-xylene and a liquid composition of 47.2% ethylbenzene 52.8% p-xylene. This indicates a relative volatility of 1.25.

EXAMPLE 4

A mixture comprising 25 grams ethylbenzene, 25 grams m-xylene, 20 grams phthalic anhydride, 20 grams maleic anhydride and 10 grams isobornyl acetate was refluxed for eleven hours in the vapor-liquid equilibrium still. Analyses showed a vapor composition of 54.1% ethylbenzene, 45.9% m-xylene and a liquid composition of 49.0% ethylbenzene and 51.0% m-xylene indicating a relative volatility of 1.22.

EXAMPLE 5

The ratios shown in Examples 3 and 4 were changed to 20 grams ethylbenzene, 20 grams p-xylene or m-xylene, 25 grams phthalic anhydride, 25 grams maleic anhydride, 10 grams isobornyl acetate and refluxed in the vapor-liquid equilibrium still for twelve hours. The relative volatility for ethylbenzene-p-xylene was 1.22, for ethylbenzene-m-xylene 1.18.

EXAMPLE 6

The ratios of ethylbenzene to p-xylene or m-xylene in Examples 3, 4 and 5 were changed to 45 grams ethylbenzene, 5 grams p-xylene; 40 grams ethylbenzene, 10 grams p-xylene; 40 grams ethylbenzene, 10 grams m-xylene; 10 grams ethylbenzene, 40 grams p-xylene and 10 grams ethylbenzene, 40 grams m-xylene, the solvent quantity being the same. The relative volatility of these mixtures was as follows:

| Hydrocarbon to Solvent Ratio | 1:1 | 1:1.5 |
|---|---|---|
| 95% EtBn:5% p-Xylene | 1.18 | 1.19 |
| 80% EtBn:20% p-Xylene | 1.20 | 1.21 |
| 80% EtBn:20% m-Xylene | 1.19 | 1.19 |
| 20% EtBn:80% p-Xylene | 1.19 | 1.21 |
| 20% EtBn:80% m-Xylene | 1.23 | 1.28 |

Every combination of successful extractive distillation agents listed in Table III was investigated under the conditions listed in Examples 3,4,5 and 6. In order to be listed in Table III, their relative volatilities must average 1.20 or higher.

EXAMPLE 7

A column consisting of two twenty-plate sections of one-inch diameter glass perforated plates equipped with a vacuum jacket was employed. The column was fitted with a Corad constant reflux ratio distilling head. Between the Corad head and the top of the column, a feed line from a constant flow pump was introduced. The stillpot was equipped with a sampling tube. The column was calibrated with a test mixture of ethylbenzene and p-xylene, which mixture possesses a relative volatility of 1.06. At a constant reflux ratio of 10 to 1, this column calibrated twelve theoretical plates. Then a run was made with a charge of approximately 20% ethylbenzene, 80% p-xylene in the stillpot. The column was operated at total reflux for about an hour, then switched to 10 to 1 reflux ratio and the pump started at a rate to deliver about one part of extractive agent to one part of ethylbenzene-p-xylene mixture being boiled up. The extractive agent in this example was 40% phthalic anhydride, 40% maleic anhydride and 20% isobornyl acetate. The following data was obtained:

| Time, hours | Overhead Comp., %EtBn | Stillpot Comp., %EtBn | Relative Volatility |
|---|---|---|---|
| 1 | 46.5 | 13.8 | 1.152 |
| 2 | 55.9 | 12.32 | 1.202 |
| 3 | 57.2 | 12.05 | 1.209 |

It will be noted that after two hours, equilibrium has been achieved and the relative volatility remains essentially constant at about 1.21. Without extractive distillation agents, it would have been 1.06.

I have shown that the proper combination of one or more compounds with phthalic anhydride and/or maleic anhydride will yield separations of ethylbenzene from p-xylene or m-xylene better than what is obtainable from any of these compounds individually.

The nature of the present invention having been described and illustrated, what I wish to claim as new and useful and secure by Letters Patent is:

1. A method for the separation of ethylbenzene from p-xylene and/or m-xylene which comprises distilling a mixture of ethylbenzene and p-xylene and/or m-xylene in the presence of an effective amount of an extractive agent comprising a mixture of phthalic anhydride and maleic anhydride.

2. The process of claim 1 in which the extractive distillation agent comprises a mixture of phthalic anhydride, maleic anhydride and one of the following; Acetonylacetone, Acetphenone, Acetyl salicylic acid, Adiponitrile, p-tertiary Amyl phenol, Anisole, Azelaic acid, Benzaldehyde, Benzoic acid, Benzonitrile, Benzophenone, Benzyl acetate, Benzyl alcohol, Butoxypropanol, Butyl benzyl phthalate, o-secondary Butyl phenol, 2-tertiary Butyl phenol, 3-tertiary Butyl phenol, 4-tertiary Butyl phenol, 1,3-Butylene glycol, beta-Butyrolactone, Carbitol acetate, Citronellyl acetate, m-Cresol o-Cresol, Cuminaldehyde, Cyanoacetic acid, Decanoic acid, Dibenzofuran, 2,6-di-tertiary Butyl-p-cresol, Dibutyl ether, 2,5-di-tertiary Butyl hydroquinone, 2,6-di-tertiary Butyl phenol, Diethyl maleate, Diethyl malonate, Diethyl phenyl malonate, Diethyl phthalate, Diethyl succinate, Diethylene glycol butyl ether acetate, Diethylene glycol dimethyl ether, Diethylene glycol methyl ether, Dihydroterpinyl acetate, Diisobutyl ketone, Dimethyl formamide, 3,5-Dimethyl phenol, Dimethyl succinate, Dimethyl sulfone, Dimethyl sulfoxide, Ethyl acetoacetate, 2-Ethyl butyric acid, 2-Ethylhexanol, Ethyl hexyl acetate, Ethyl phenyl acetate, Ethyl salicylate, p-Ethyl phenol, Ethylene glycol butyl ether, Ethylene glycol ethyl ether acetate, Ethylene glycol mono stearate, Fenchyl alcohol, 9-Fluorenone, 1,6-Hexanediol, Hexahydrophthalic acid anhydride, Hexyl acetate, Hexylene glycol, Hexylene glycol diacetate, Hydro bis phenol A, Isoborneol, Isobornyl acetate, Isobornyl methyl ether, Isooctanol, Isophorone, Isopropyl myristate, Linalyl acetate, Menthyl acetate, Methyl benzoate, 4-Methyl benzophenone-2-carboxylic acid, Methyl hexanoate, Myristic acid, m-Nitroacetophenone, p-Nitroacetophenone, m-Nitrobenzaldehyde, m-Nitrobenzoic acid, 5-Nitroisophthalic acid diethyl ester, p-Nitrophenol, p-Nitrophenylacetic acid, p-Nitrotoluene, Nonanic acid, 2-Octanone, Phenethyl alcohol, Phenol, Phenyl acetate, Phenyl acetic acid, 2-Phenylphenol, 3-Phenyl-1-propanol, Propionic anhydride, Propoxypropanol, Propyl-p-hydroxybenzoate, Sebacic acid,, Succinic anhydride, Succinimide, Sulfolane, Sulfolene, Tetrahydrofurfuryl alcohol, 2,2',4,4'-Tetrahydroxybenzophenone, p-Tolualdehyde, Tributylphosphate, Triethylene glycol diacetate, o-Toluic acid.

3. The process of claim 1 in which the extractive distillation agent comprises a mixture of phthalic anhydride and benzoic acid.

4. The process of claim 1 in which the extractive distillation agent comprises a mixture of phthalic anhydride, benzoic acid and one of the following; Diisononyl phthalate, Diethylene glycol ethyl ether acetate, Methyl salicylate, Diisobutyl ketone, Diisononyl phthalate, Diisobutyl phthalate, Diethyl maleate, Methyl hexanoate, Isobutyl isobutyrate, Dimethylsulfoxide, Dimethylformamide, n-Octanol, n-Decanol, Ethyl acetoacetate, 4-Nitrophenol, 4-tertiary Butyl phenol, Dimethylsulfone, 4-tertiary Butyl catechol, 2-Phenylphenol.

5. The process of claim 1 in which the extractive distillation agent comprises a mixture of phthalic anhydride, salicylic acid and one of the following; Diisobutyl phthalate, Methyl hexanoate, Ethylene glycol phenyl ether, and the pair Dimethylsulfoxide, Methyl hexanoate.

6. The process of claim 1 in which the extractive distillation agent comprises a mixture of benzoic acid, maleic anhydride and one of the following; Diethyl maleate, Methyl hexanoate, Acetophenone, Triethylene glycol diacetate, Diethylene glycol hexyl ether, Dimethyl phthalate, Dibutyl phthalate, Diisononyl adipate, Tributyl phosphate, n-Octanol, 1,6-Hexanediol, 4-secondary Butyl phenol, p-Ethylbenzaldehyde.

7. The process of claim 1 in which the extractive distillation agent comprises a mixture of benzoic acid, maleic anhydride, phthalic anhydride and one of the following; Glycerol triacetate, Diethyl maleate, Phenyl acetate, Ethylene glycol diacetate, Dimethyl adipate, Ethylene glycol methyl ether acetate, Diethylene glycol diethyl ether, Tributyl phosphate, Tricresyl phosphate, Catechol, Ethyl acetoacetate, Phenol, o-Cresol, 2,6-Dibutyl phenol, Diisobutyl ketone, Tetrahydrofurfuryl alcohol.

8. The process of claim 1 in which the extractive distillation agent comprises a mixture of maleic anhydride and one of the following pairs; m-Nitrobenzoic acid & Butoxypropanol, 4-tertiary Butyl catechol & Nonanic acid, 2-Phenylphenol & Isobornyl acetate, p-Nitrophenol & Myristic acid.

9. The process of claim 1 in which the extractive distillation agent comprises a mixture of phthalic anhydride and one of the following; Levulinic acid, m-Nitrobenzoic acid, Acetonylacetone.

10. The process of claim 1 in which the extractive distillation agent comprises a mixture of phthalic anhydride and one of the following pairs; Acetylsalicylic acid & Isophorone, Azelaic acid & Isophorone, o-Toluic acid & Phenol.

11. The process of claim 1 in which the extractive distillation agent comprises a mixture of hexahydrophthalic anhydride, maleic anhydride and one of the following; Butoxypropanol, n-Octanol.

12. The process of claim 1 in which the extractive distillation agent comprises a mixture of maleic anhydride, azelaic acid and one of the following; Ethylphenyl acetate, Phenylacetic acid.

13. The process of claim 1 in which the extractive distillation agent comprises a mixture of Phthalic anhydride, Benzoic acid, Dimethylsulfoxide and Methyl hexanoate.

14. The process of claim 1 in which the extractive distillation agent comprises a mixture of Phthalic anhydride, Succinic acid, Ethylene glycol diacetate and Carbitol acetate.

15. The process of claim 1 in which the extractive distillation agent comprises a mixture of Benzoic acid, Succinic anhydride and Diethyl maleate.

16. The process of claim 1 in which the extractive distillation agent comprises a mixture of Phthalic anhydride, Methyl p-hydroxybenzoate and Diethyl oxalate.

17. The process of claim 1 in which the extractive distillation agent comprises a mixture of Benzoic acid, Salicylic acid and Tributyl phosphate.

18. The process of claim 1 in which the extractive distillation agent comprises a mixture of Maleic anhydride and m-Nitroacetophenone.

* * * * *